(12) United States Patent
Klein et al.

(10) Patent No.: US 9,943,320 B2
(45) Date of Patent: Apr. 17, 2018

(54) FEMORAL EXPLANT DEVICE

(71) Applicant: Zimmer, Inc., Warsaw, IN (US)

(72) Inventors: Gregg Klein, Livingston, NJ (US);
Harlan Levine, Tenafly, NJ (US);
Timothy A. Hoeman, Morris Plains, NJ (US); Ray Zubok, Midland Park, NJ (US); Robert G. Deluca, Bethlehem, PA (US); Natalia Fridshtand, Ringwood, NJ (US); Scott V. Cron, Wayne, NJ (US)

(73) Assignee: Zimmer, Inc., Warsaw, IN (US)

( * ) Notice: Subject to any disclaimer, the term of this patent is extended or adjusted under 35 U.S.C. 154(b) by 839 days.

(21) Appl. No.: 14/300,639

(22) Filed: Jun. 10, 2014

(65) Prior Publication Data
US 2014/0371750 A1    Dec. 18, 2014

Related U.S. Application Data

(60) Provisional application No. 61/834,095, filed on Jun. 12, 2013, provisional application No. 61/899,606, filed on Nov. 4, 2013.

(51) Int. Cl.
| | |
|---|---|
| *A61B 17/16* | (2006.01) |
| *A61B 17/17* | (2006.01) |
| *A61B 17/15* | (2006.01) |
| *A61F 2/46* | (2006.01) |
| *A61B 90/00* | (2016.01) |

(52) U.S. Cl.
CPC ........ *A61B 17/1675* (2013.01); *A61B 17/155* (2013.01); *A61B 17/1604* (2013.01); *A61B 17/1764* (2013.01); *A61F 2/461* (2013.01); *A61B 2090/034* (2016.02); *A61F 2002/4623* (2013.01); *A61F 2002/4624* (2013.01)

(58) Field of Classification Search
CPC ............ A61B 17/3468; A61B 17/1604; A61B 17/1675; A61B 17/1659
See application file for complete search history.

(56) References Cited

U.S. PATENT DOCUMENTS

| | | | |
|---|---|---|---|
| 3,803,667 A | 4/1974 | Rose | |
| 4,409,973 A * | 10/1983 | Neufeld ................ | A61B 17/15 606/178 |
| 5,702,460 A | 12/1997 | Carls et al. | |

(Continued)

FOREIGN PATENT DOCUMENTS

| | | |
|---|---|---|
| EP | 3007654 B1 | 5/2017 |
| WO | WO-2014200984 A1 | 12/2014 |

OTHER PUBLICATIONS

"European Application Serial No. 14734702.5, Response filed Aug. 22, 2016 to Communication pursuant to Rules 161(1) and 162 EPC dated Feb. 10, 2016", 11 pgs.

(Continued)

*Primary Examiner* — Andrew Yang
(74) *Attorney, Agent, or Firm* — Schwegman Lundberg & Woessner, P.A.

(57) ABSTRACT

An apparatus for removal of a femoral implant may include a handle portion and a cutting blade opposite the handle portion. The cutting blade may include a cutting edge, wherein the cutting edge includes a non-linear shape to substantially match at least a portion of a profile of the femoral implant to be removed.

20 Claims, 20 Drawing Sheets

(56) References Cited

U.S. PATENT DOCUMENTS

| | | |
|---|---|---|
| 6,110,175 A | 8/2000 | Scholl |
| 2012/0089147 A1 | 4/2012 | Kuczynski |

OTHER PUBLICATIONS

"International Application Serial No. PCT/US2014/041677, International Preliminary Report on Patentability dated Dec. 23, 2015", 11 pgs.

"International Application Serial No. PCT/US2014/041677, International Search Report dated Oct. 17, 2014", 7 pgs.

"International Application Serial No. PCT/US2014/041677, Invitation to Pay Additional Fees and Partial Search Report dated Aug. 25, 2014", 6 pgs.

"International Application Serial No. PCT/US2014/041677, Written Opinion dated Oct. 17, 2014", 9 pgs.

\* cited by examiner

US 9,943,320 B2

FEMORAL EXPLANT DEVICE

CLAIM OF PRIORITY

This application claims the benefit of U.S. Provisional Patent Application Ser. No. 61/834,095, filed on Jun. 12, 2013, and also claims the benefit of U.S. Provisional Patent Application Ser. No. 61/899,606, filed on Nov. 4, 2013, the benefit of priority of each of which is claimed hereby, and each of which are incorporated by reference herein in its entirety.

BACKGROUND

Orthopedic prostheses are commonly utilized to prepare and/or replace damaged bone and tissue in the human body. For example, a prosthetic knee implant can be used to restore natural knee function by repairing damaged or diseased articular surfaces of a femur, a tibia, or both. Knee implants can include a femoral component implanted on the distal end of a femur, which articulates with a natural tibia or with a tibial component implanted on the corresponding proximal end of tibia. The femoral and tibial components can cooperate to restore the function of healthy natural knee. Hip implants can include a femoral implant component and an acetabular cup component for placement in the hip socket. A prosthetic implant may need to be replaced. The replacement procedure can be difficult and can result in bone loss for the patient.

OVERVIEW

This document discusses systems, devices and methods for improved explant of prosthetic implants. An apparatus example may include a handle portion and a cutting blade opposite the handle portion. The cutting blade may include a cutting edge having a non-linear shape to substantially match at least a portion of a profile of the femoral implant to be removed. A method example may include positioning a guiding structure into the femoral bone using a placement guide arranged at an end of a femoral bone, guiding a handled cutting blade, using the guiding structure, into position at an interface of the femoral bone and a femur-contacting surface of the femoral implant, and applying force to the handled cutting blade to separate the femoral implant from the femoral bone.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As explained previously herein, orthopedic prostheses can include multiple components. For example, knee implants typically include a femoral component and can also include a tibial component. The implant components may include material (e.g., Trabecular Metal™) or structures to promote this bone growth for strong attachment to the implant. However, sometimes the implant or a component of the implant needs replacing. Because bone tissue has infiltrated the promoting surface of the implant, the implant can be difficult to remove. The present inventors have recognized a need for improvement for devices and methods for explant of prosthetic components that minimize bone loss.

Figure 1A:
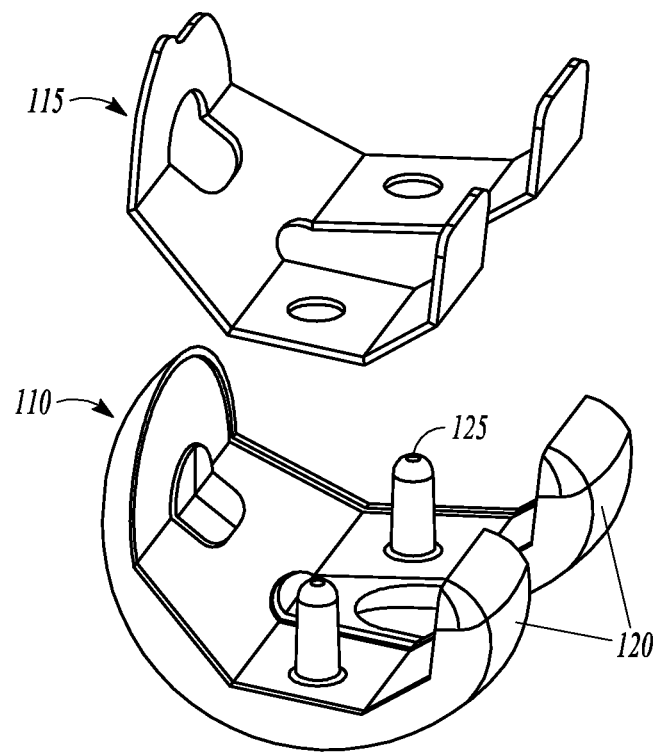
FIGS. 1A, 1B illustrate portions of an example of a femoral implant.
Figure 1B:
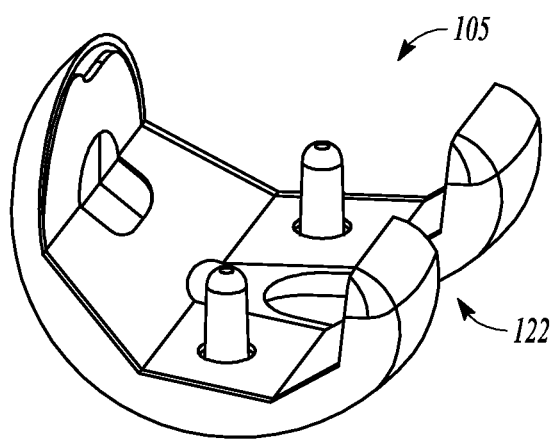

FIGS. 1A and 1B illustrate portions of an example of a femoral implant 105. The femoral implant 105 includes a substrate 110 and a plate component 115. The substrate 110 includes an articulating surface 120. The articulating surface 120 can include a lateral condyle and a medial condyle. The lateral condyle and the medial condyle can be configured for articulation with a natural tibia or prosthetic tibial component. The femoral component 105 can include a trochlear gap 122 to accommodate a natural or prosthetic patella.

The substrate 110 may also include one or more fixation pegs 125 for placement in the distal end of a femur. The plate component 115 can be bonded to the substrate 110 to form the femoral implant 105. The plate component 115 includes a femur contacting surface that can include material to promote bone ingrowth and reduce slippage of the femoral implant.

Figure 2:
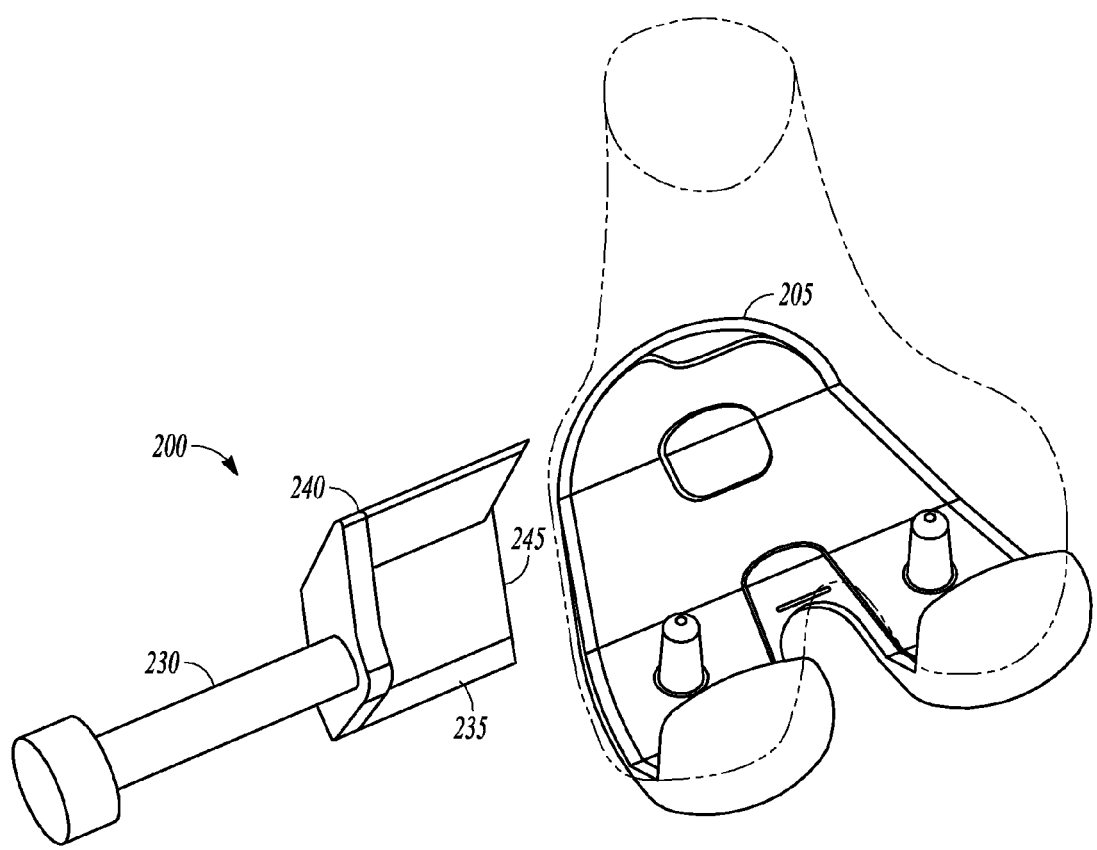
FIG. 2 is an illustration of an example of a device for removal of a femoral implant.

FIG. 2 is an illustration of an example of a device 200 for removal of a femoral implant 205. The device 200 includes a handle portion 230 and a cutting blade 235 opposite the handle portion 230. The device 200 can include a bolster 240 arranged between the cutting blade 235 and the handle portion 230. The bolster 240 can prevent slippage if force is applied to the device 200 by hand and may provide structural reinforcement of the cutting blade. The cutting blade 235 includes a cutting edge 245. The cutting edge 245 includes a non-linear shape that substantially matches at least a portion of the profile of the femoral implant 205 to be removed. The cutting edge 245 separates bone tissue from the femur contacting surface of the femoral implant 205 as force is applied. In certain examples, the cutting edge 245 includes a bevel on one side.

As shown in FIG. 2, the femur contacting surface of the femoral implant includes multiple planes, and the cutting edge 245 of the device includes multiple planes to match some or all of the planes of the femoral implant 205. The cutting blade 235 is shown also having multiple planes. In the example shown, the cutting blade 235 matches approximately two and a half planes of the femur-contacting surface. At least a first plane and second plane of the cutting blade 135 intersect at an angle to substantially match an angle of the profile of the femoral implant 205. However, the cutting blade and the cutting edge do not both need to substantially match the shape of the femoral implant.

Figure 3:
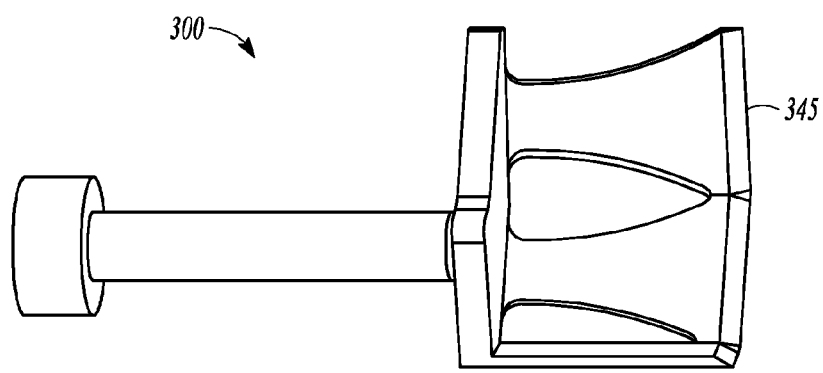
FIG. 3 is an illustration of another example of a device for removal of a femoral implant.

FIG. 3 is an illustration of another example of a device 300 for removal of a femoral implant. In the example, the cutting edge 345 of the device 300 includes multiple planes to match some or all of the planes of the femoral implant, but do not match the shape of the femoral implant. In the example shown, the planes of the cutting blade can be angled away from the planes of the femoral implant.

Figure 4:
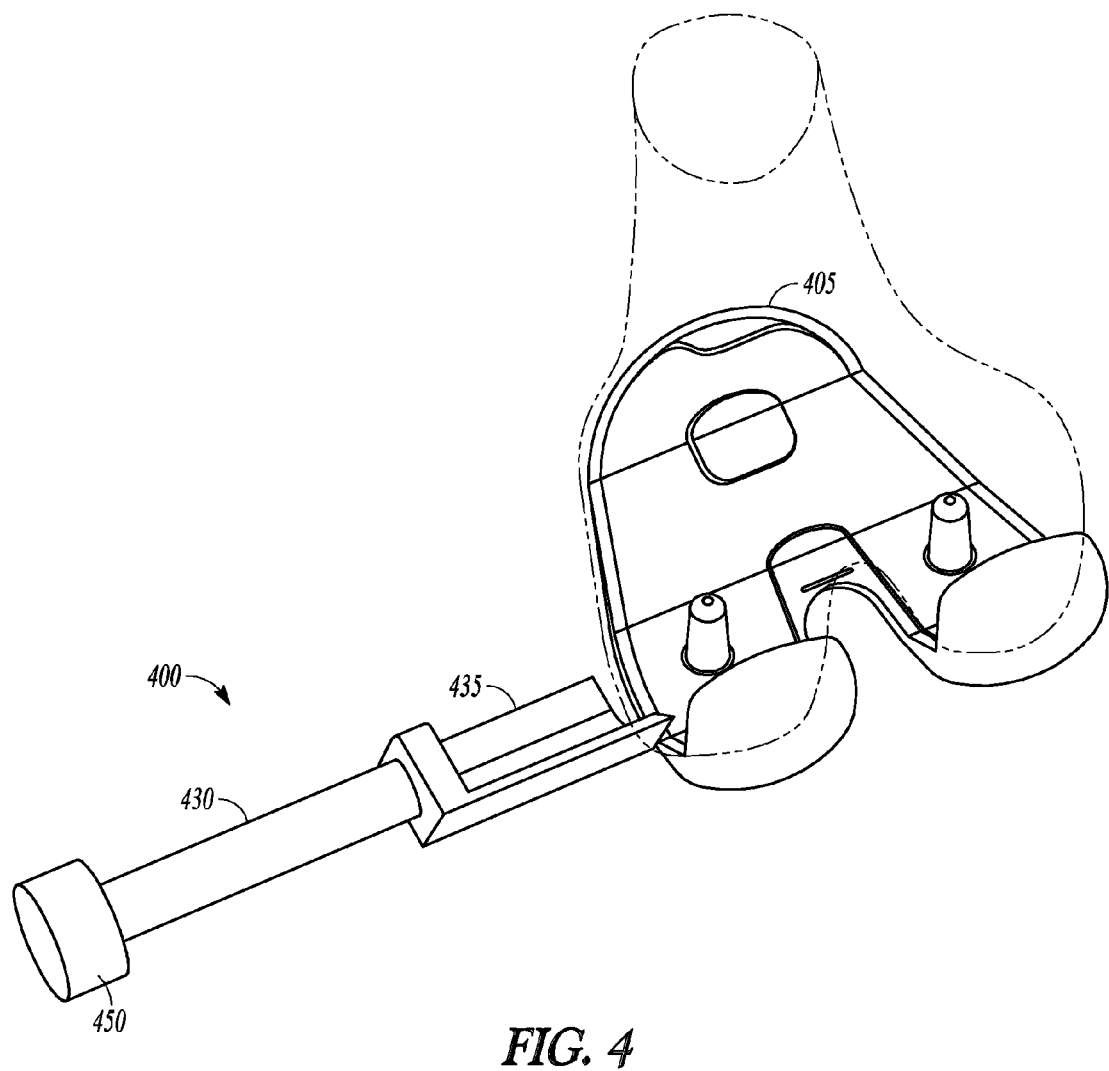
FIG. 4 is an illustration of still another example of a device for removal of a femoral implant.

FIG. 4 is an illustration of still another example of a device 400 for removal of a femoral implant 405. The cutting blade 435 includes multiple planes to match a different set of planes of the femoral implant 405 from what is shown in FIG. 2. In some examples, the cutting blade 435 includes a number of planes to match the number of planes of the femur contacting surface of the femoral implant 405. The handle portion 430 can include a head 450 opposite the cutting blade 435 and configured by shape and size to receive impact force, such as from a mallet or air hammer for example.

Figure 5:
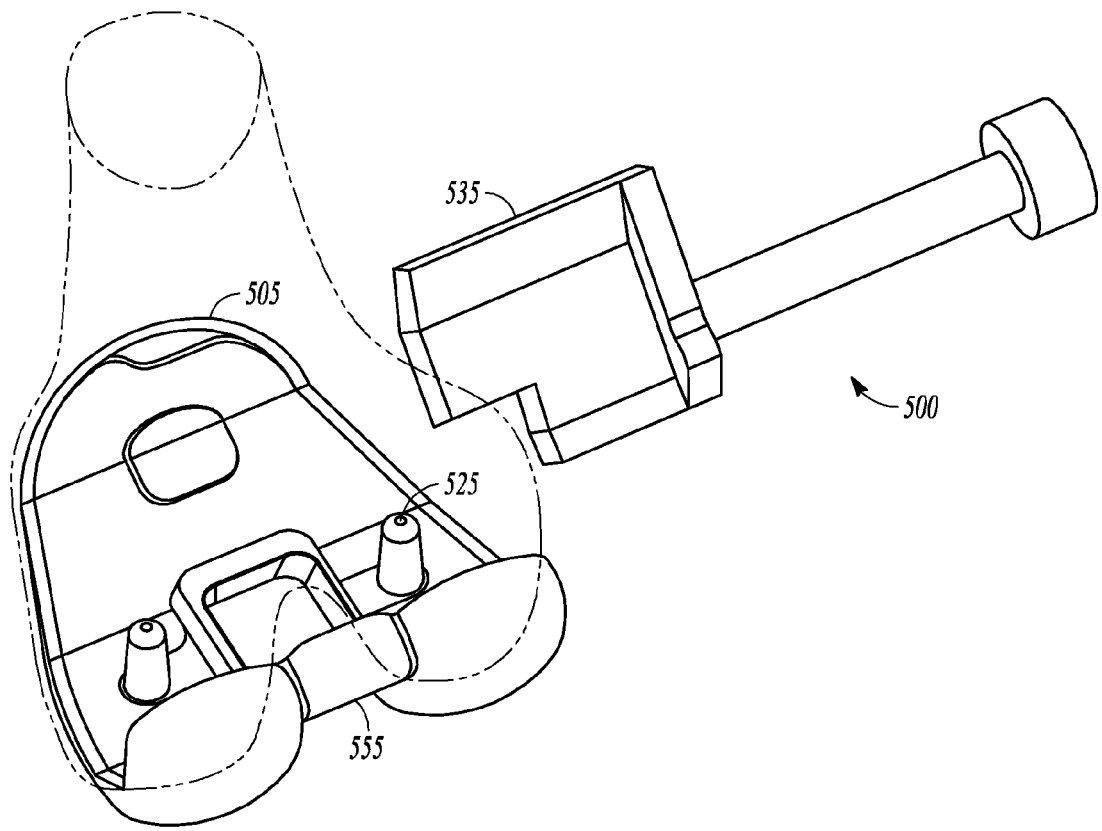
FIG. 5 is an illustration of still another example of a device for removal of a femoral implant.

FIG. 5 is an illustration of still another example of a device 500 for removal of a femoral implant 505. Again the cutting blade 535 includes a plurality of planes to substantially match a portion of the femoral implant 505. In the example shown, the planes of the cutting blade 535 can have different lengths. The femoral implant 505 may include fixation posts 525 and may include a box-like projection 555. A cutting blade with different lengths can be useful to avoid structural features of the femoral implant 505 like the fixation posts 525 and the box-like projection 555.

Figure 6:
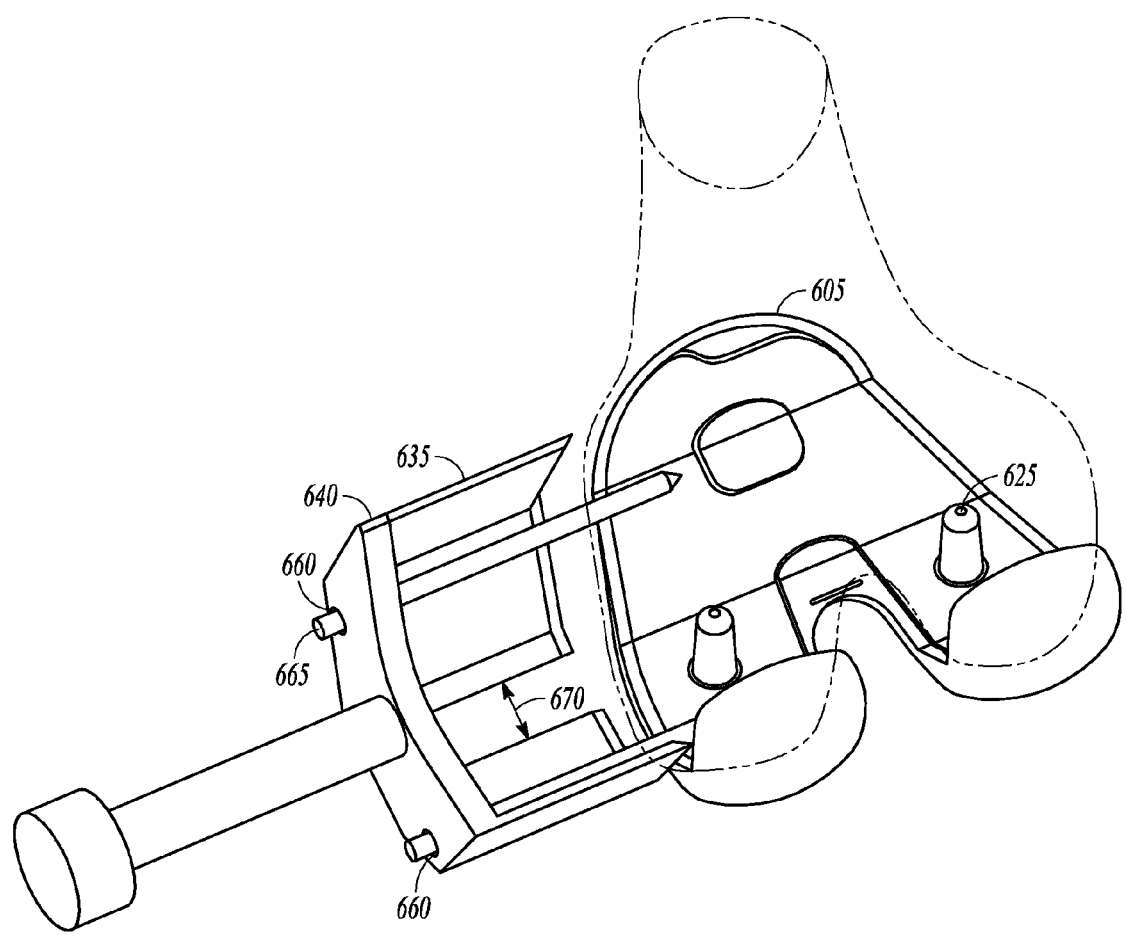
FIG. 6 is an illustration of still another example of a device for removal of a femoral implant.

FIG. 6 is an illustration of still another example of a device 600 for removal of a femoral implant 605. In the example shown, bolster 640 includes multiple guide openings 660 (e.g., holes) arranged to receive a guiding structure 665. The guiding structure 665 guides the cutting blade 635 into position at the femoral implant 605. In certain examples, the bolster 640 intersects the cutting blade substantially orthogonally, and includes guide openings 660 to receive a plurality of pins positioned to guide the cutting blade 635 into position at an interface of a femoral bone and a femur-contacting surface of the femoral implant 605. In certain examples, the bolster 640 includes guide openings 660 to receive a plurality of Kirschener wires, or K-wires, placed in the femoral bone.

The bolster 640 and the cutting blade 635 can be formed as a single unit that is connectable to the handle portion 630. In this way, different cutting blades can be attached to the same handle. In certain examples, the handle portion 630 and the bolster 640 are a single unit that is connectable to a cutting blade 635 that can be replaceable. In certain examples, all of the elements are individually connectable units, and the bolster 640 is connectable to the cutting blade 635 and the handle portion 630 is connectable to the bolster 640.

The example cutting blade 635 shown includes planes (e.g., five planes) to substantially match the planes of the femur contacting surface of the femoral implant 605. The cutting blade 635 includes a gap 670. The gap 670 can be included in one or more of the planes to avoid a feature of the femoral implant 605 (e.g., a fixation post 625 or other projection).

Figure 7:
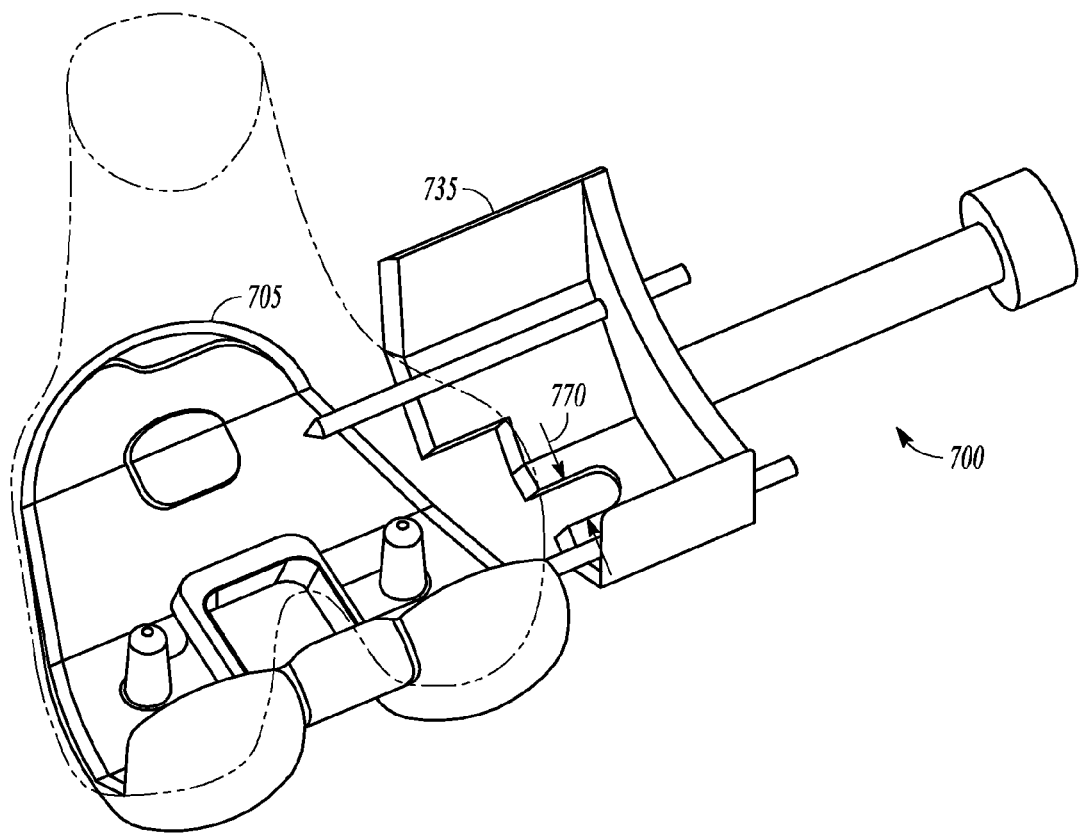
FIG. 7 is an illustration of still another example of a device for removal of a femoral implant.

FIG. 7 is an illustration of still another example of a device 700 for removal of a femoral implant 705. The example shows that the device 700 can be configured to cut on the medial and lateral sides of the femur. In certain examples, the cutting blade 735 includes several features already described such as a gap 770 and planes of multiple lengths. In certain examples, the cutting blade 735 can be interchangeable to accommodate a change between medial and lateral sides and to include a shape to avoid features of the femoral implant 705.

Figure 8:
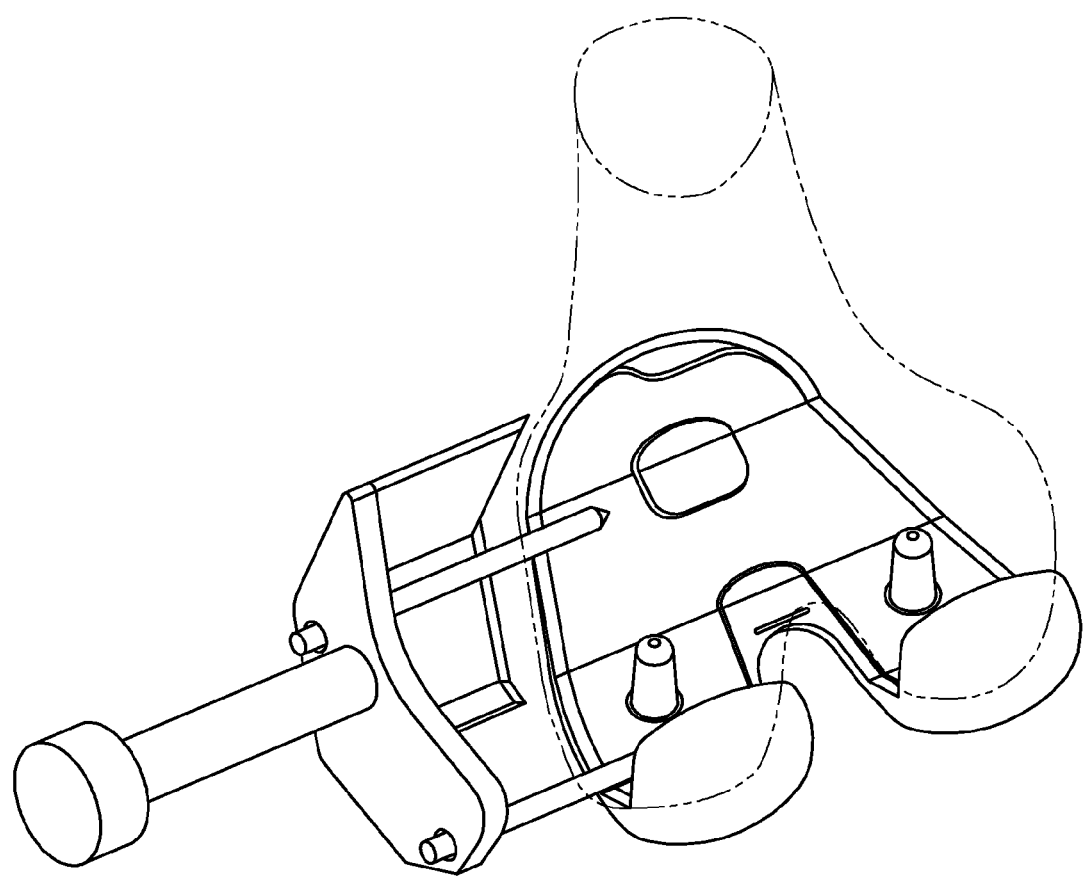
FIGS. 8, 9, 10 and 11 illustrate additional examples of devices for removal of a femoral implant.
Figure 9:
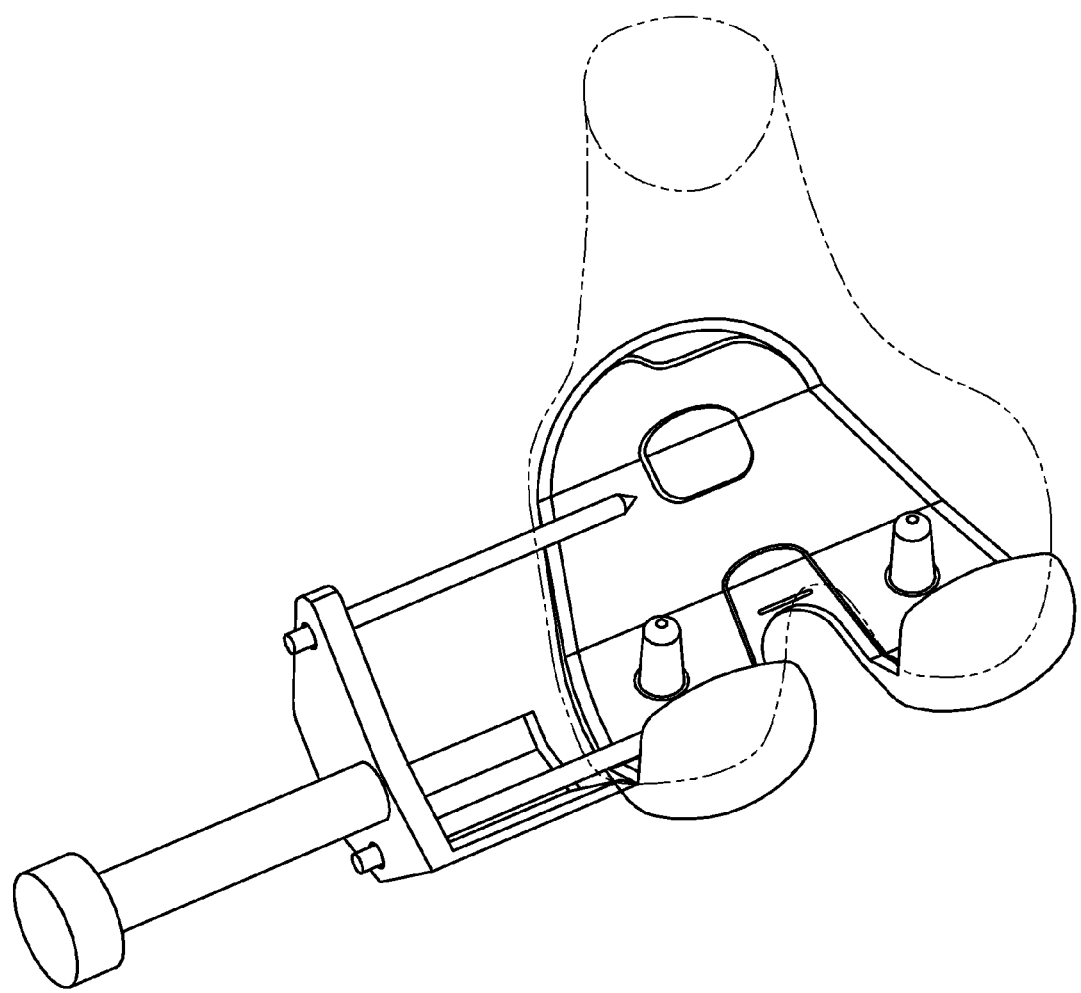

FIGS. 8 through 11 illustrate additional examples of a device for removal of a femoral implant. The Figures show both medial and lateral examples and include combinations of the different features described. In the example of FIG. 8, a bolster intersects the cutting blade substantially orthogonally, and the bolster includes guide openings to receive a plurality of pins positioned to guide the cutting blade into position at an interface of a femoral bone and a femur-contacting surface of the femoral implant. The cutting blade includes a plurality of planes to substantially match a portion of the femoral implant. In the example of FIG. 9, the device includes a cutting blade having a plurality of planes to substantially match a different portion of the femoral implant than the example of FIG. 8.

Figure 10:
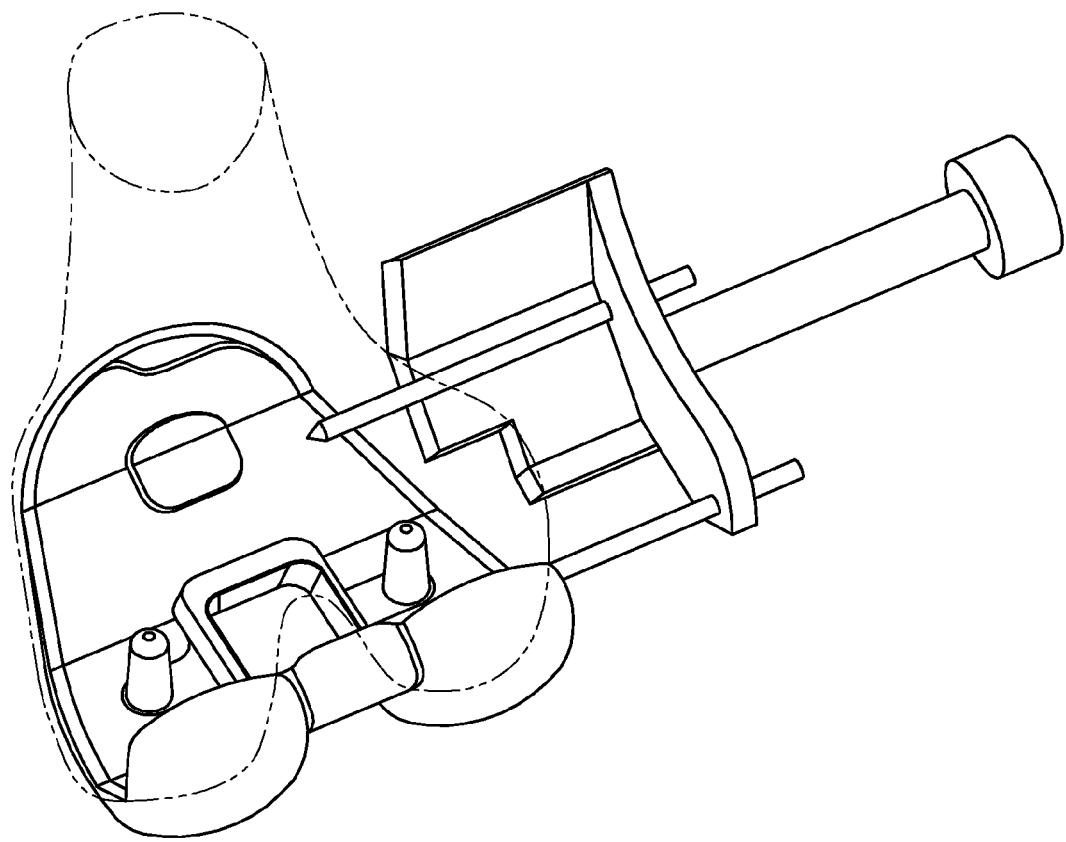

In the example of FIG. 10, a bolster intersects the cutting blade substantially orthogonally, and includes guide openings to receive a plurality of pins positioned to guide the cutting blade into position at an interface of a femoral bone and a femur-contacting surface of the femoral implant. The cutting blade includes a plurality of planes to substantially match a portion of the femoral implant. The planes can include different lengths to accommodate any pins or box-like projections of the femoral implant.

Figure 11:
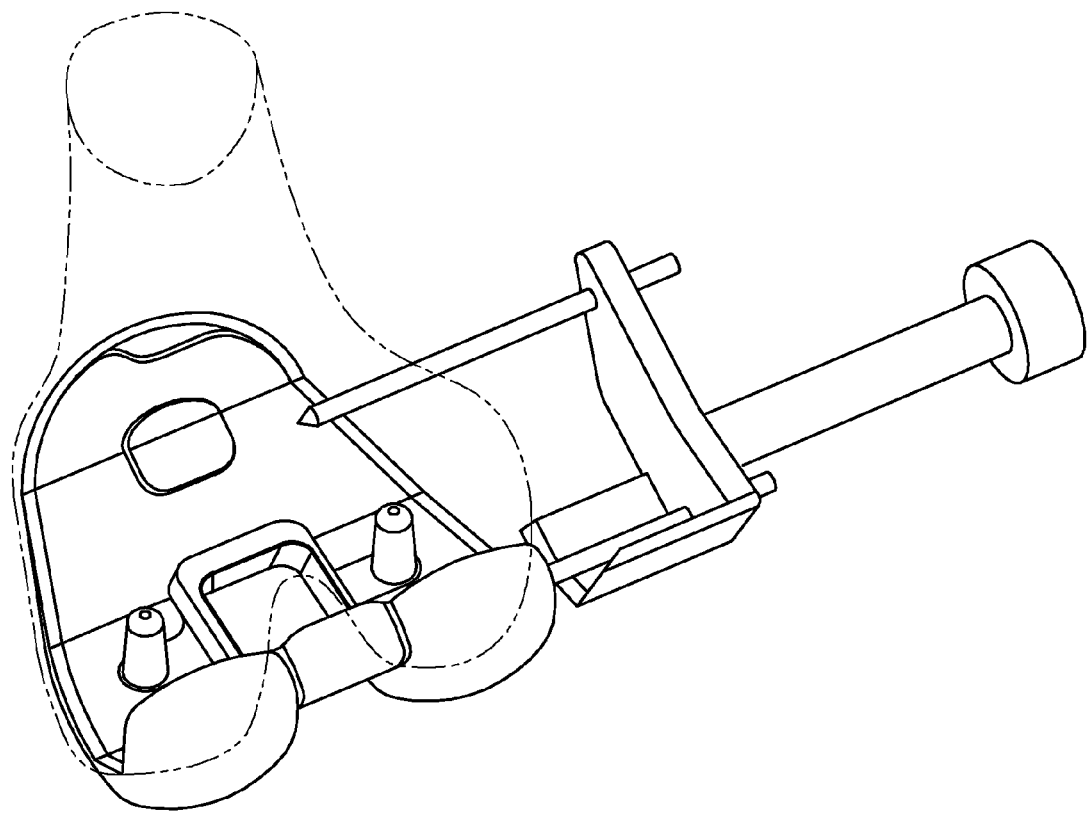

In the example of FIG. 11, the device includes a cutting blade having a plurality of planes to substantially match a different portion of the femoral implant than the example of FIG. 10. The cutting blade includes planes having a length to avoid the box-like projection of the femoral implant. As in the example of FIG. 7, the cutting blade of the examples of FIGS. 8-11 can be interchangeable to accommodate a change between medial and lateral sides and to include a shape to avoid features of the femoral implant.

Figure 12:
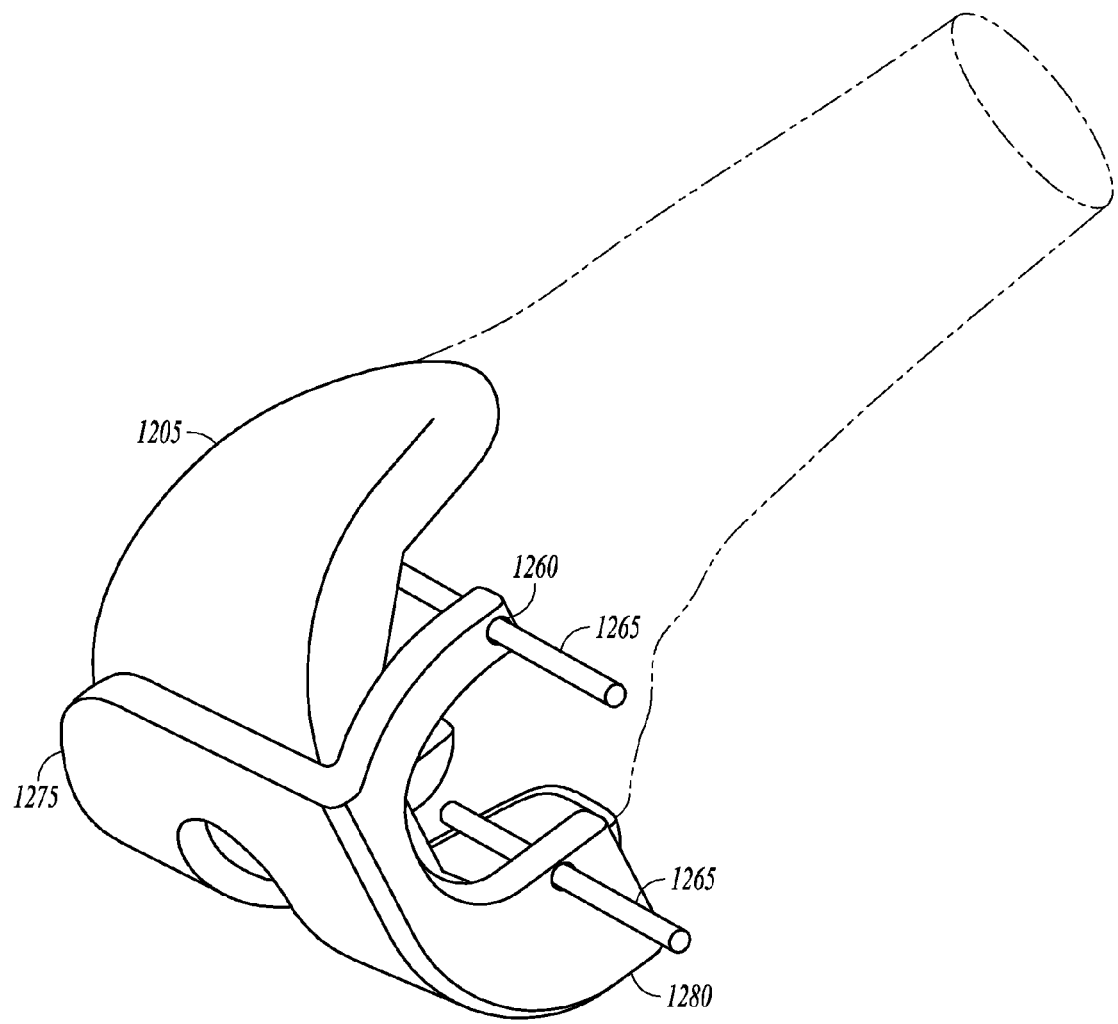
FIGS. 12 and 13 illustrate examples of a placement guide for positioning a guiding structure at femoral bone for removal of a femoral implant.

FIG. 12 illustrates an example of a placement guide 1275 for positioning a guiding structure 1265 into femoral bone for removal of a femoral implant 1205. The placement guide 1275 is shown placed over the femoral implant 1205, and the placement guide 1275 may be size-specific to the femoral implant 1205. The placement guide 1275 can include a plate 1280 having openings 1260 to receive a guiding structure for positioning in the femoral bone. Some examples of the guiding structure can include pins, K-wires and bone screws. A different placement guide can be used for positioning a guiding structure at the medial side and at the lateral side. In certain examples, the openings 1260 in the plate 1280 are used as a drill guide for placement of the guiding structure.

Figure 13:
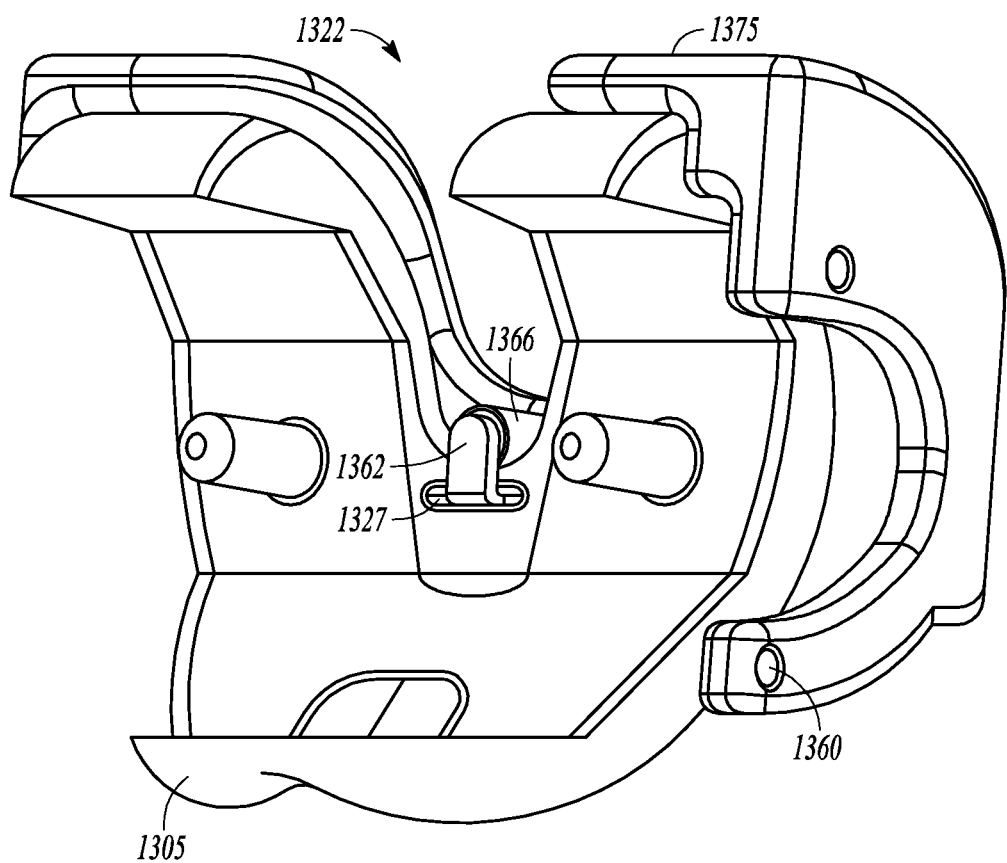

FIG. 13 illustrates another example of a placement guide 1375 useful for positioning a guiding structure at femoral bone for removal of a femoral implant 1305. The placement guide 1375 may include openings 1360 to receive a guiding structure for positioning in the femoral bone. The Figure shows an example of a mechanism for attaching the placement guide 1375 to the femoral implant 1305. The mechanism can include a tab 1362 included with the placement guide 1375 and a slot 1327 included with the femoral implant 1305. The tab 1362 can include a raised edge configured by any combination of position, shape and size to fit into the slot 1327 to attach the placement guide 1375 to the femoral implant 1305. The tab 1362 may be arranged at the end of a post 1366 that extends into trochlear gap 1322 of the femoral implant 1305.

Figure 14A:
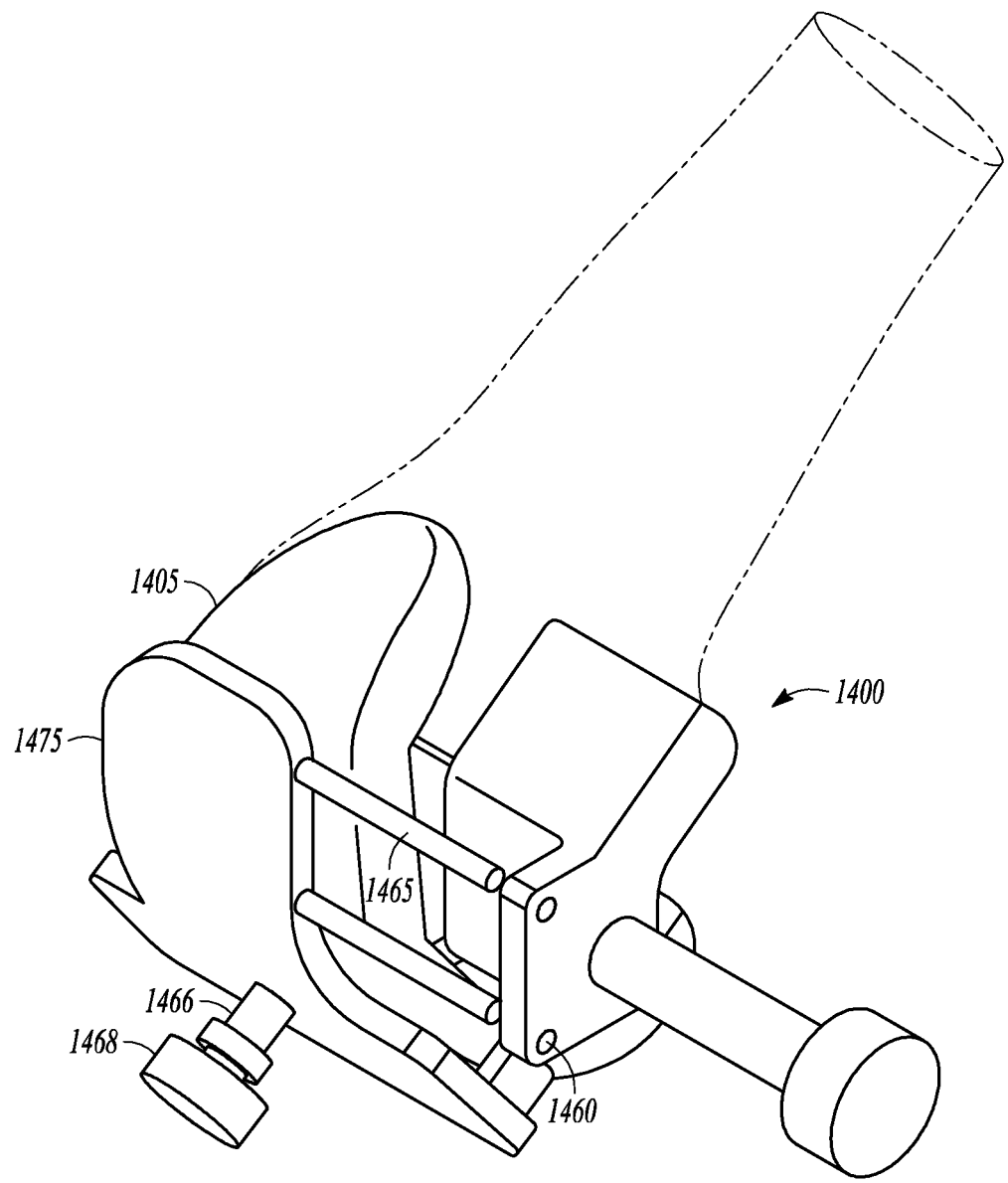
FIGS. 14A and 14B illustrate another example of a placement guide for positioning a guiding structure at femoral bone.
Figure 14B:
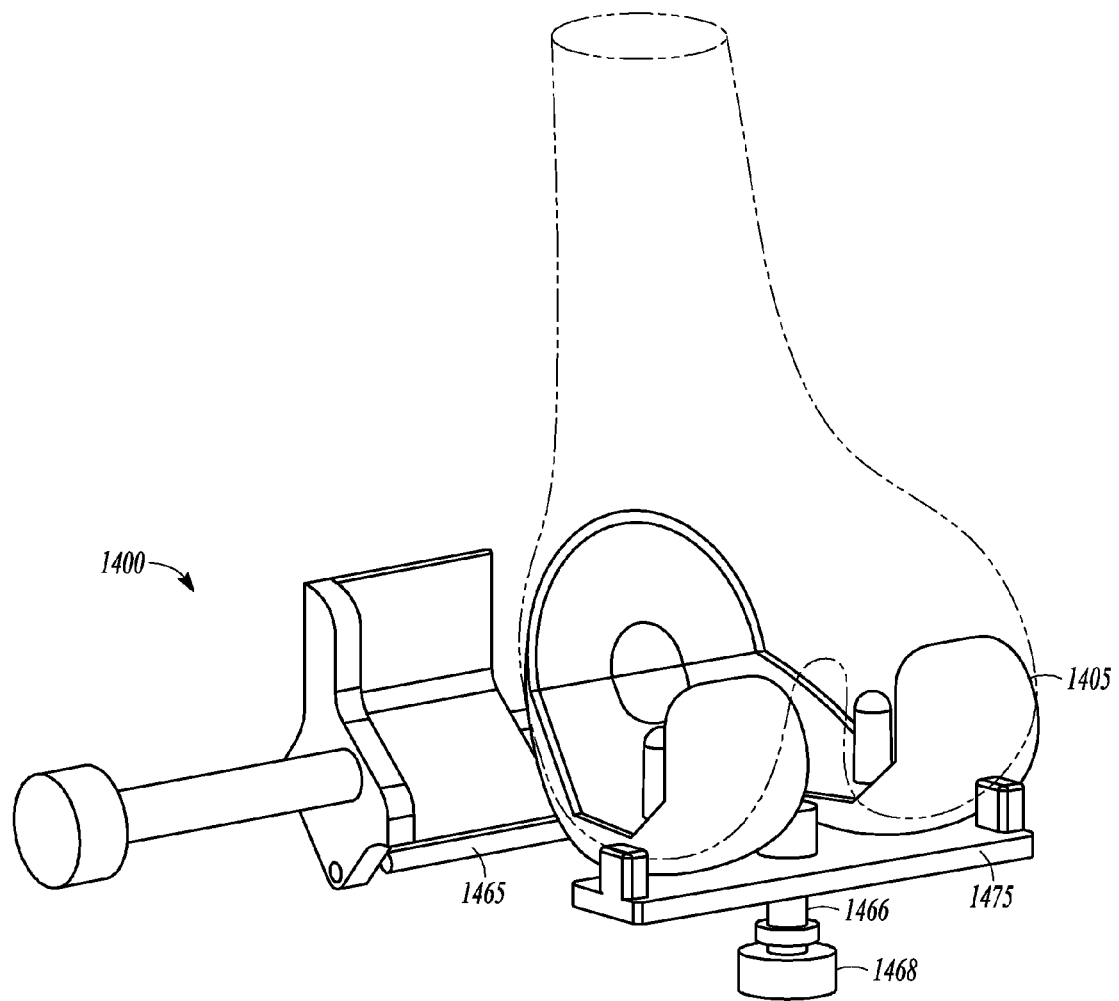

FIGS. 14A and 14B illustrate still another example of a placement guide 1475 for positioning a guiding structure at femoral bone for removal of a femoral implant 1405. FIG. 14A shows that the guiding structure 1465 is included with the placement guide 1475 and can include one or more pins or wires. FIG. 14A also shows another example of a device 1400 for removal of the femoral implant 1405. The device 1400 includes a bolster that has guide openings 1460 to receive the guiding structure 1465 to position (e.g., by sliding) the device 1400 at the femoral bone. Thus, drilling to place the guiding structure is not required in this example. FIG. 14B shows another view of the placement guide 1475 and the device 1400 for removal of the femoral implant.

Figure 15:
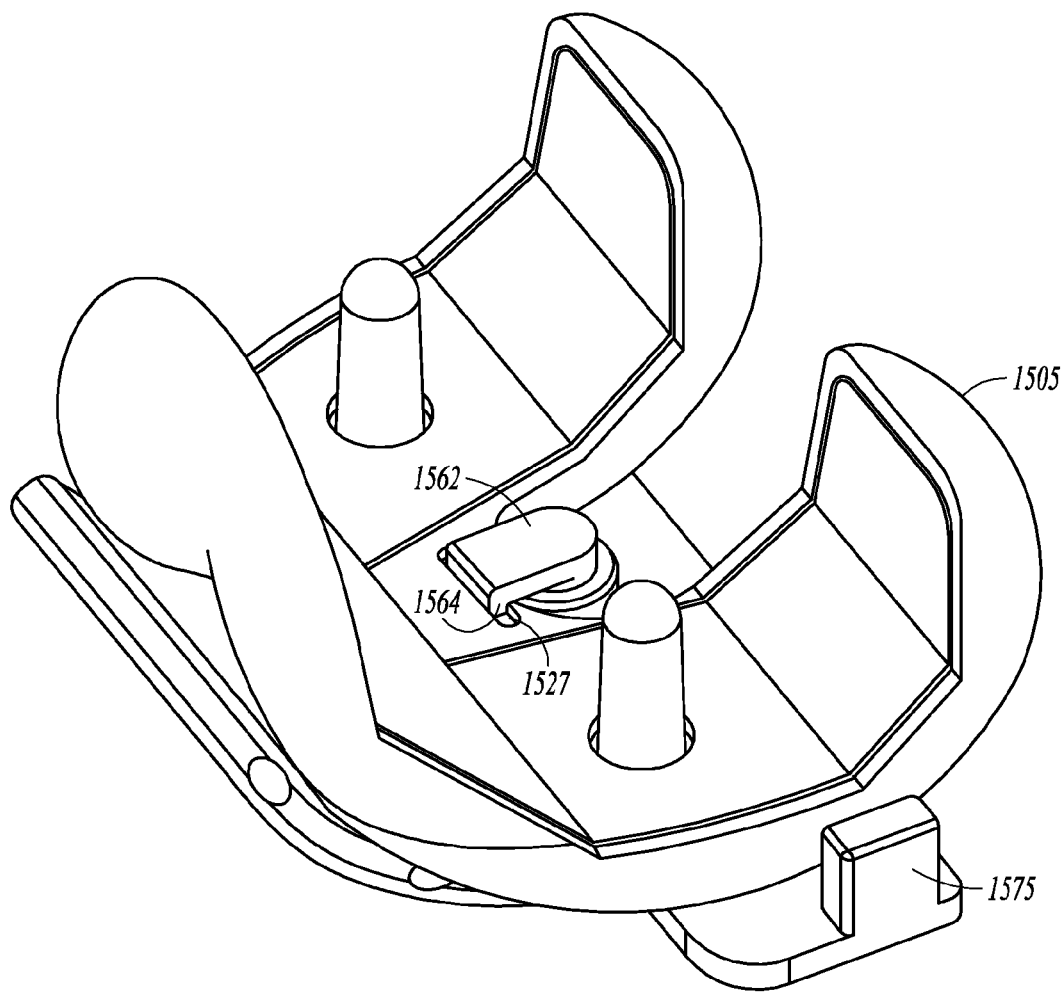
FIGS. 15 and 16 illustrate portions of further examples of a placement guide for positioning a guiding structure at femoral bone for removal of a femoral implant.

FIG. 15 illustrates still another example of portions of a placement guide 1575 for positioning a guiding structure at femoral bone for removal of a femoral implant 1505. The placement guide 1575 may include the guiding structure as is shown in FIGS. 14A and 14B, but a guiding structure is not shown in FIG. 15 to simplify the Figure. As in the example of FIG. 13, the example of FIG. 15 can include a mechanism for attaching the placement guide 1575 to the femoral implant 1505. The mechanism can include a tab 1562 included with the placement guide 1575 and a slot 1527 included with the femoral implant 1505. The tab 1562 can include a raised edge 1564 that fits into the slot 1527 to attach the placement guide 1575 to the femoral implant 1505.

Figure 16:
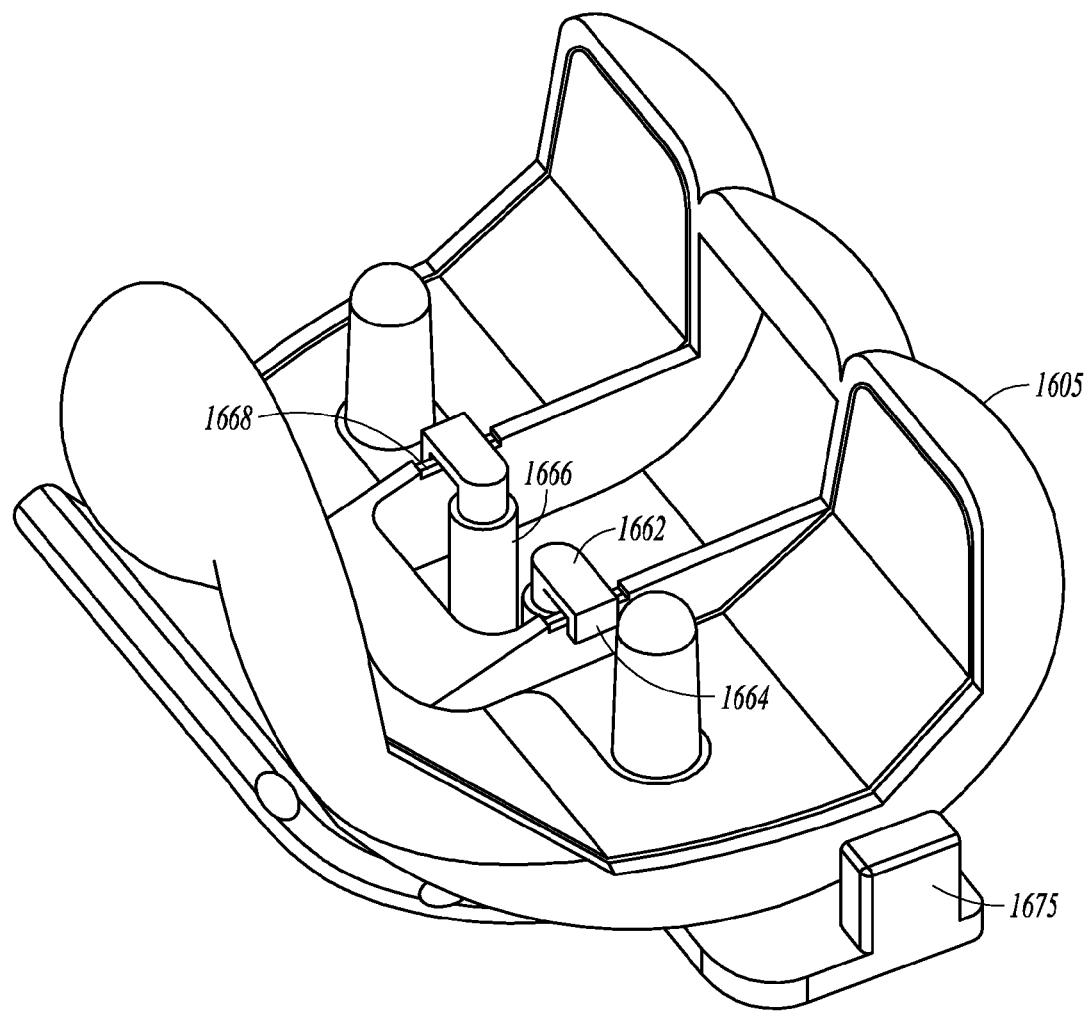

FIG. 16 illustrates still another example of portions of a placement guide 1675 for positioning a guiding structure at femoral bone for removal of a femoral implant 1605. As in the example of FIG. 15, the placement guide 1675 may include a guiding structure that is not shown to simplify the Figure. FIG. 16 shows another example of a mechanism to attach the placement guide 1675 to the femoral implant 1605. The mechanism can include multiple posts 1666 arranged substantially orthogonal to a surface of the placement guide 1675 to extend into the trochlear opening of the femoral implant 1605. The posts 1666 can include a tab 1662 having a protruding edge to extend over a ridge of the femoral implant 1605 to attach the placement guide 1675. The ridge of the femoral implant 1605 may include a cutout 1668 to receive the tab 1662.

Returning to FIGS. 14A and 14B, the placement guide 1475 can include a knob 1468 that is attached to a post 1466 that includes a tab (not shown). The tab can be used to attach the placement guide 1475 to the femoral implant 1405 as shown in the example of FIG. 13.

Figure 17:
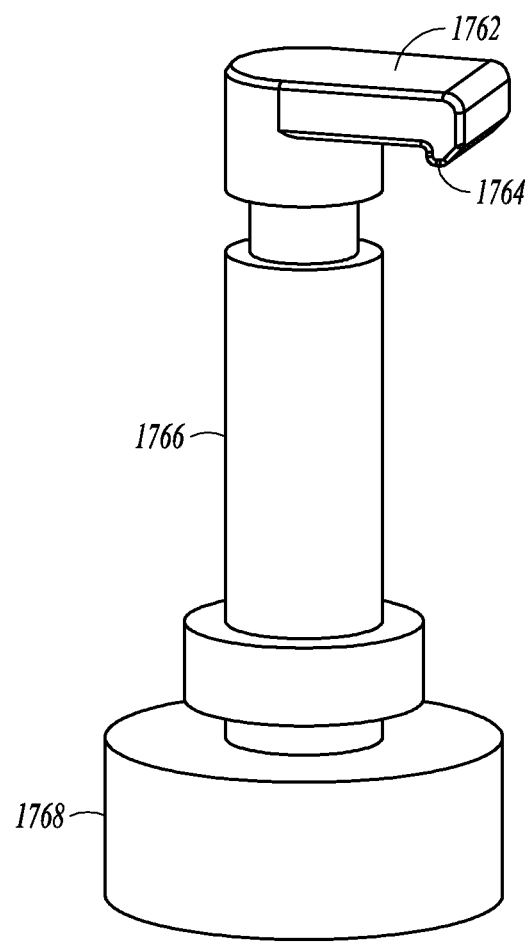
FIG. 17 shows an example of a mechanism for attaching a placement guide to a femoral implant.

FIG. 17 shows an isolated view of an example of a mechanism for attaching the placement guide to the femoral implant. The mechanism includes a tab 1762 attached to post 1766 that is attached to a knob 1768. The tab 1762 can include a raised edge 1764 that fits into a slot of the femoral implant. In some examples, the tab 1762 is threaded onto the post 1766, and the mechanism can be tightened by rotating the knob 1768 to secure the placement guide and the femoral implant.

Figure 18:
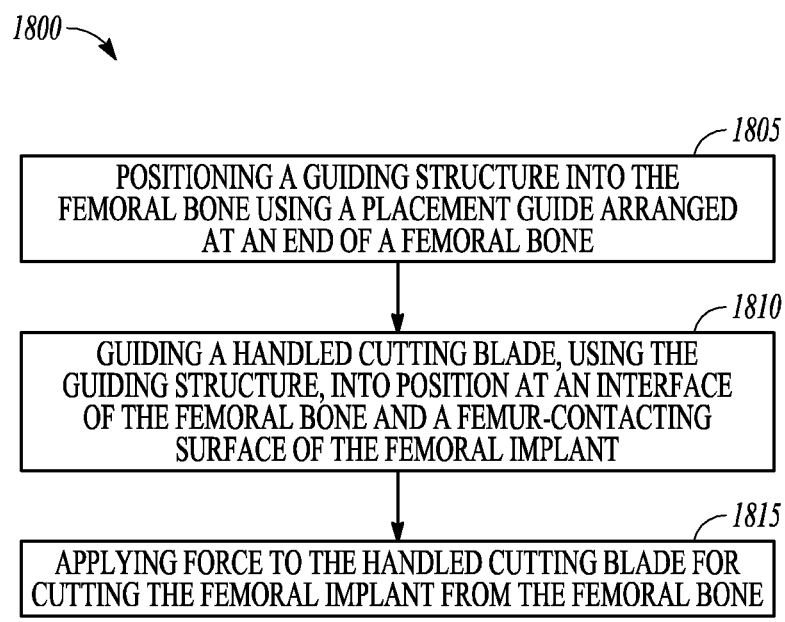
FIG. 18 shows a flow diagram of a method for removal of a femoral implant.

FIG. 18 shows a flow diagram of a method 1800 for removal of a femoral implant. At block 1805, a guiding structure is positioned into the femoral bone using a placement guide arranged at an end of a femoral bone (e.g., a distal end). The placement guide may be a size-specific placement guide that can be arranged at the end of the femoral bone, such as the placement guide example shown in FIGS. 12 through 16.

At block 1810, a handled cutting blade is guided into position using the guiding structure. In some examples, a guiding structure is placed into a guide opening of the handled cutting blade, and the handled cutting blade can be slid into position using the guiding structure. The handled cutting blade is positioned at an interface of the femoral bone and a femur-contacting surface of the femoral implant. The handled cutting blade may be positioned at a medial side of the femur or at the lateral side of the femur. The handled cutting blade may include a cutting edge that matches the shape of the interface.

At block 1815, force is applied to the handled cutting blade for cutting the femoral implant from the femoral bone. The force may be applied by hand, with a mallet, or an air hammer. Because the cutting edge substantially matches the shape of the interface and may be aligned at the interface using a guide, bone loss from the cutting or separating is minimized. In certain examples, the cutting edge can include a gap, and the guiding structure positions the gap to avoid a feature of the femoral implant. The cutting may separate the femoral implant from the femoral bone, or additional cutting with another handled cutting blade to facilitate the separation.

Figure 19:
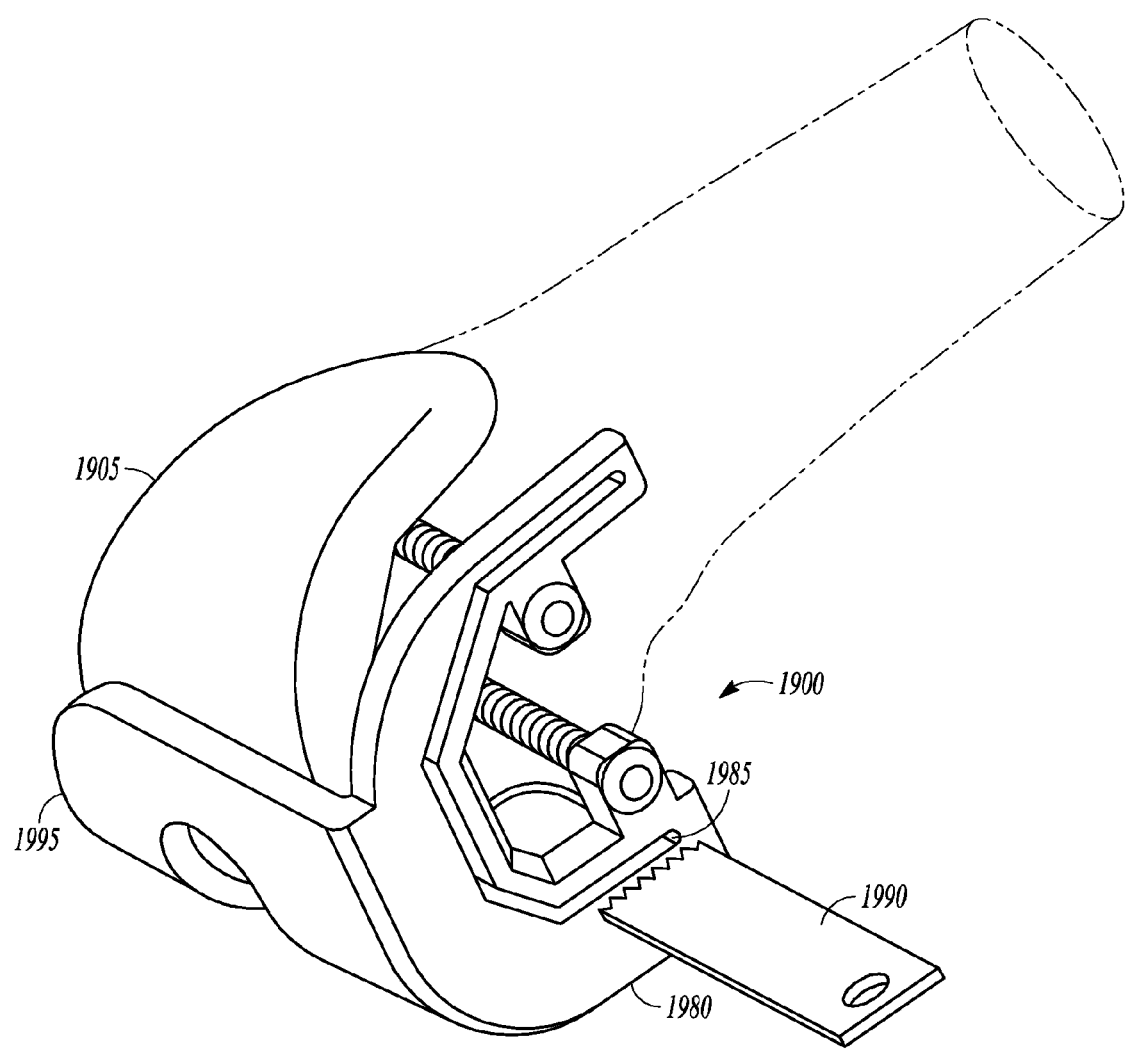
FIG. 19 illustrates another example of a device for removal of a femoral implant.

FIG. 19 illustrates another example of a device 1900 for removal of a femoral implant 1905. The device 1900 can include a cutting guide plate 1980. The cutting guide plate 1980 includes a cutting guide slot 1985. The cutting guide slot 1985 has a slot width sufficient to receive a cutting blade 1990. In the example shown, the cutting guide slot 1985 can be wide enough to receive a saw blade. The saw blade may be attachable to a powered saw (e.g., a reciprocating saw). In certain instances, the cutting guide slot 1985 can be configured (e.g., by shape and size) to receive a flexible cutting blade that bends with the shape of the cutting guide slot 1985 (e.g., an osteotome with a flexible cutting blade).

The device 1900 also may include at least one placement guide opening that is arranged on the cutting guide plate 1980 to receive a guiding structure 1965. In the example shown, the device 1900 includes two placement guide openings to receive two bone screws. In certain examples, the guiding structure includes K-wires. The at least one guiding structure is configured to position the cutting guide slot at the interface between the femoral bone and the femur-contacting surface of the femoral implant. The cutting guide slot 1985 includes a slot path length that has a non-linear shape to substantially match at least a portion of a profile of the interface between the femoral bone and the femur-contacting surface of the femoral implant 1905. A user (e.g., a surgeon) may cut along the slot path to separate the femoral implant from the femoral bone.

In certain examples, the device 1900 includes a plurality of placement guide openings arranged to receive a guiding structure configured to position the side surface at a lateral side or a medial side of the femoral bone. The user may cut along the slot path with the device 1900 positioned at a first side (e.g., lateral side) of the femur, and reposition the device or position a second device on the second side of the femur and cut along the slot path on the second side to complete separating the femoral implant from the femoral bone. The device 1900 may include a second surface 1995 substantially orthogonal to the cutting guide plate 1980 to provide stability. The device 1900 may be size-specific to facilitate alignment with the profile of the interface between the femoral bone and the femur-contacting surface of the femoral implant 1905.

Figure 20:
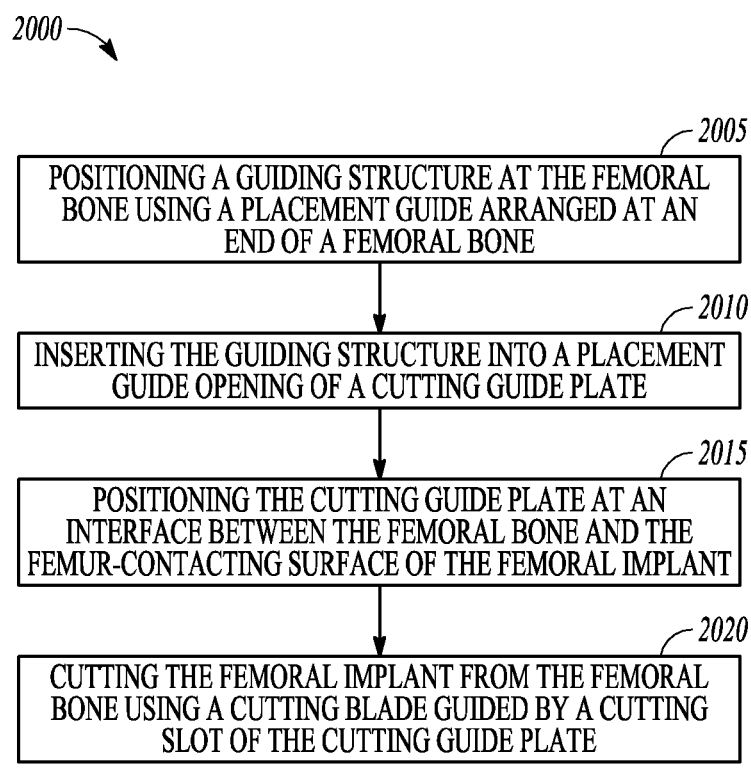
FIG. 20 shows a flow diagram of a method for removal of a femoral implant.

FIG. 20 shows a flow diagram of a method 2000 for removal of a femoral implant. At block 2005, a guiding structure is positioned at the femoral bone using a placement guide arranged at an end of a femoral bone. The placement guide may be a drill guide and the guiding structure may be placed into the femoral bone. At block 2010, the guiding structure is inserted into a placement guide opening of a cutting guide plate.

At block 2015, the cutting guide plate is positioned, according to the guiding structure, at an interface between the femoral bone and the femur-contacting surface of the femoral implant. In certain examples, the cutting guide plate can be positioned by sliding the cutting guide plate along the guiding structure. At block 2020, the femoral implant can be cut from the femoral bone using a cutting blade guided by a cutting slot of the cutting guide plate. A saw blade or flexible cutting blade can be used to cut along the femoral bone and femur-contacting surface interface. The cutting may separate the femoral implant from the femoral bone or additional cutting may be necessary. Additional cutting may be facilitated by positioning of another cutting guide.

The devices and methods described herein provide for removal of prosthetic implants, including those implants designed to promote bone growth for strong attachment to the implant, while reducing or minimizing bone loss from the removal.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure.

This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus for removal of a femoral implant, the apparatus comprising:
   a cutting device comprising:
      a handle portion, and
      a cutting blade opposite the handle portion and including a cutting edge, wherein the cutting edge includes a non-linear shape to substantially match at least a portion of a profile of the femoral implant to be removed, the cutting edge further defining a gap positioned to avoid a feature of the femoral implant; and
   a placement guide configured to be placed over the femoral implant and receive the cutting device, the placement guide including an engagement feature sized for engagement with a trochlear gap of the femoral implant, the engagement feature configured to removably couple the placement guide to the femoral implant.

2. The apparatus of claim 1, wherein the cutting blade includes a plurality of planes, wherein a first plane and a second plane of the plurality of planes intersect at an angle to substantially match an angle of the profile of the femoral implant to be removed.

3. The apparatus of claim 2, wherein the first plane and the second plane of the plurality of planes have different lengths.

4. The apparatus of claim 1, including a bolster arranged between the cutting blade and the handle portion, wherein the bolster includes a plurality of guide openings arranged to receive a guiding structure configured to guide the cutting blade into position at the femoral implant.

5. The apparatus of claim 1, including a bolster that intersects the cutting blade substantially orthogonally, wherein the bolster includes a plurality of guide openings arranged to receive a plurality of K-wires.

6. The apparatus of claim 1, including a bolster that intersects the cutting blade substantially orthogonally, wherein the bolster includes a plurality of guide openings arranged to receive a plurality of pins positioned to guide the cutting blade into position at an interface of a femoral bone and a femur-contacting surface of the femoral implant.

7. The apparatus of claim 1, wherein the cutting blade includes a number of planes to match a number of planes of a femur contacting surface of the femoral implant.

8. The apparatus of claim 1, including a bolster arranged between the cutting blade and the handle portion, wherein the bolster and cutting blade are formed as a single unit connectable to the handle portion.

9. The apparatus of claim 1, wherein the handle portion includes a head opposite the cutting blade and configured to receive impact force.

10. An apparatus for removal of a femoral implant, the apparatus comprising:
   a cutting device comprising:
      a handle portion, and
      a cutting blade opposite the handle portion and including a cutting edge, wherein the cutting edge includes a non-linear shape to substantially match at least a portion of a profile of the femoral implant to be removed;
   a placement guide configured to be placed over the femoral implant and receive the cutting device, the placement guide including an engagement feature sized for engagement with a trochlear gap of the femoral implant, the engagement feature configured to removably couple the placement guide to the femoral implant; and
   a bolster arranged between the cutting blade and the handle portion, wherein the bolster and handle portion are formed as a single unit connectable to the cutting blade.

11. The apparatus of claim 10, wherein the cutting blade includes a plurality of planes, wherein a first plane and a second plane of the plurality of planes intersect at an angle to substantially match an angle of the profile of the femoral implant to be removed.

12. The apparatus of claim 11, wherein the first plane and the second plane of the plurality of planes have different lengths.

13. The apparatus of claim 10, wherein the cutting blade includes a number of planes to match a number of planes of a femur contacting surface of the femoral implant.

14. The apparatus of claim 10, wherein the cutting edge includes a gap, wherein the gap is positioned to avoid a feature of the femoral implant.

15. An apparatus for removal of a femoral implant, the apparatus comprising:
   a cutting device comprising:
      a handle portion, and
      a cutting blade opposite the handle portion and including a cutting edge, wherein the cutting edge includes a non-linear shape to substantially match at least a portion of a profile of the femoral implant to be removed;
   a placement guide configured to be placed over the femoral implant receive the cutting device, the placement guide including an engagement feature sized for engagement with a trochlear gap of the femoral implant, the engagement feature configured to removably couple the placement guide to the femoral implant; and
   a bolster arranged between the cutting blade and the handle portion, wherein the bolster is connectable to the cutting blade and the handle portion is connectable to the bolster.

16. The apparatus of claim 15, wherein the cutting blade includes a plurality of planes, wherein a first plane and a second plane of the plurality of planes intersect at an angle to substantially match an angle of the profile of the femoral implant to be removed.

17. The apparatus of claim 16, wherein the first plane and the second plane of the plurality of planes have different lengths.

18. The apparatus of claim 15, wherein the cutting blade includes a number of planes to match a number of planes of a femur contacting surface of the femoral implant.

19. The apparatus of claim 15, wherein the cutting edge includes a gap, wherein the gap is positioned to avoid a feature of the femoral implant.

20. An apparatus for removal of a femoral implant, the apparatus comprising:
   a cutting device comprising:
      a handle portion, and
      a cutting blade opposite the handle portion and including a cutting edge, wherein the cutting edge includes a non-linear shape to substantially match at least a portion of a profile of the femoral implant to be removed; and
   a placement guide configured to be placed over the femoral implant and receive the cutting device, the placement guide including an engagement feature sized for engagement with a trochlear gap of the femoral implant, the engagement feature configured to removably couple the placement guide to the femoral implant;
   wherein the handle portion includes a head opposite the cutting blade and configured to receive impact force.

* * * * *

UNITED STATES PATENT AND TRADEMARK OFFICE
CERTIFICATE OF CORRECTION

PATENT NO. : 9,943,320 B2
APPLICATION NO. : 14/300639
DATED : April 17, 2018
INVENTOR(S) : Klein et al.

Page 1 of 1

It is certified that error appears in the above-identified patent and that said Letters Patent is hereby corrected as shown below:

In the Claims

In Column 10, Line 19, in Claim 15, after "implant", insert --and--

Signed and Sealed this
Eleventh Day of June, 2019

Andrei Iancu
*Director of the United States Patent and Trademark Office*